(12) United States Patent
Abunassar

(10) Patent No.: US 11,801,140 B2
(45) Date of Patent: Oct. 31, 2023

(54) CATHETER ASSEMBLY WITH COAPTATION AID AND METHODS FOR VALVE REPAIR

(71) Applicant: EVALVE, INC., Santa Clara, CA (US)

(72) Inventor: Chad Abunassar, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 226 days.

(21) Appl. No.: 17/096,638

(22) Filed: Nov. 12, 2020

(65) Prior Publication Data

US 2021/0145583 A1    May 20, 2021

Related U.S. Application Data

(60) Provisional application No. 62/935,227, filed on Nov. 14, 2019.

(51) Int. Cl.
*A61F 2/24* (2006.01)
*A61B 17/00* (2006.01)
(Continued)

(52) U.S. Cl.
CPC ...... *A61F 2/2466* (2013.01); *A61B 17/00234* (2013.01); *A61B 2017/00323* (2013.01);
(Continued)

(58) Field of Classification Search
CPC ...... A61F 2/2466; A61F 2/246; A61F 2/2463; A61F 2/2475; A61F 2/2478;
(Continued)

(56) References Cited

U.S. PATENT DOCUMENTS

| 3,378,010 A | 4/1968 | Codling et al. |
| 3,874,388 A | 4/1975 | King et al. |

(Continued)

FOREIGN PATENT DOCUMENTS

| CA | 2 296 317 C | 1/2009 |
| CN | 107738378 A | 2/2018 |

(Continued)

OTHER PUBLICATIONS

International Search Report and Written Opinion dated Feb. 25, 2021 in International Application No. PCT/US2020/060233.
(Continued)

*Primary Examiner* — Erich G Herbermann
(74) *Attorney, Agent, or Firm* — SLEMAN & LUND LLP

(57) ABSTRACT

Catheter assembly with a coaptation aid for repair of leaflets of a heart valve includes an elongate catheter shaft adapted to be positioned transvascularly proximate a heart valve and a lever coupled to the catheter shaft. The lever has a hinge to transition the lever between an elongate delivery configuration generally aligned longitudinally with the catheter shaft and a deployed configuration extending transversely from the catheter shaft. The lever also includes an atraumatic tip at a distal end thereof and adapted to contact a distal side of a native leaflet of the heart valve when the catheter shaft is positioned proximate the heart valve and the lever is in the deployed configuration, and an actuation assembly coupled to the lever to remotely transition the lever between the delivery configuration and the deployed configuration. Method for fixation of native leaflets of a heart valve using the catheter assembly also disclosed.

27 Claims, 14 Drawing Sheets

(51) Int. Cl.
*A61B 17/08* (2006.01)
*A61M 25/00* (2006.01)

(52) U.S. Cl.
CPC .............. *A61B 2017/00367* (2013.01); *A61B 2017/00867* (2013.01); *A61B 2017/081* (2013.01); *A61F 2/246* (2013.01); *A61M 2025/0042* (2013.01)

(58) Field of Classification Search
CPC .... A61F 2/2457; A61F 2/2454; A61F 2/2469; A61F 2/24; A61F 2/2403; A61F 2/2439; A61F 2002/249; A61B 17/00234; A61B 17/1285; A61B 17/122; A61B 17/1227; A61B 17/128; A61B 2017/00323; A61B 2017/00367; A61B 2017/00867; A61B 2017/081; A61B 2017/00783; A61B 2017/00862; A61B 2017/2825; A61B 2017/2926; A61M 2025/0042
See application file for complete search history.

(56) References Cited

U.S. PATENT DOCUMENTS

| | | |
|---|---|---|
| 4,007,743 A | 2/1977 | Blake |
| 4,055,861 A | 11/1977 | Carpentier et al. |
| 4,327,736 A | 5/1982 | Inoue |
| 4,340,091 A | 7/1982 | Skelton et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 5,002,562 A | 3/1991 | Oberlander |
| 5,069,679 A | 12/1991 | Taheri |
| 5,098,440 A | 3/1992 | Hillstead |
| 5,125,895 A | 6/1992 | Buchbinder et al. |
| 5,147,370 A | 9/1992 | McNamara et al. |
| 5,171,259 A | 12/1992 | Inoue |
| 5,222,963 A | 6/1993 | Brinkerhoff et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,843,178 A | 12/1998 | Vanney et al. |
| 5,849,019 A | 12/1998 | Yoon |
| 5,855,601 A | 1/1999 | Bessler et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,346,074 B1 | 2/2002 | Roth |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 7,011,669 B2 | 3/2006 | Kimblad |
| 7,074,206 B2 | 7/2006 | Lee et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 * | 6/2007 | Lucatero ............ A61B 17/0487 606/191 |
| 7,556,632 B2 | 7/2009 | Zadno |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,828,766 B2 | 11/2010 | Durcan |
| 7,972,323 B1 | 7/2011 | Bencini et al. |
| 7,981,139 B2 | 7/2011 | Martin et al. |
| 8,052,638 B2 | 11/2011 | Lee et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,394,055 B2 | 3/2013 | Durcan |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 9,132,259 B2 | 9/2015 | Lin et al. |
| 9,510,829 B2 | 12/2016 | Goldfarb et al. |
| 10,076,415 B1 | 9/2018 | Metchik et al. |
| 10,086,175 B2 | 10/2018 | Torres et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 * | 3/2019 | Metchik .................. A61F 2/246 |
| 10,238,493 B1 | 3/2019 | Metchik et al. |

(56) References Cited

U.S. PATENT DOCUMENTS

| | | |
|---|---|---|
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 2002/0013571 A1 | 1/2002 | Goldfarb et al. |
| 2002/0183787 A1 | 12/2002 | Wahr et al. |
| 2003/0047437 A1 | 3/2003 | Stankevitch |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2005/0267493 A1 | 12/2005 | Schreck et al. |
| 2007/0038293 A1 | 2/2007 | Goar St. et al. |
| 2007/0197858 A1 | 8/2007 | Goldfarb et al. |
| 2013/0073034 A1 | 3/2013 | Wilson |
| 2015/0057704 A1 | 2/2015 | Takahashi |
| 2015/0080624 A1 | 3/2015 | Gephart |
| 2015/0182223 A1* | 7/2015 | Ketai ............... A61F 2/246 606/151 |
| 2016/0067459 A1 | 3/2016 | Williams et al. |
| 2016/0339204 A1 | 11/2016 | Williams et al. |
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2017/0336070 A1 | 11/2017 | Inskip |
| 2018/0021133 A1* | 1/2018 | Barbarino ......... A61F 2/2463 623/2.37 |
| 2018/0036119 A1 | 2/2018 | Wei et al. |
| 2018/0092661 A1 | 4/2018 | Prabhu |
| 2018/0133008 A1 | 5/2018 | Kizuka |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0275486 A1 | 9/2019 | Peltekis |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | |
|---|---|---|
| CN | 108285800 A | 7/2018 |
| EP | 0 558 031 B1 | 9/1993 |
| EP | 0662503 A1 | 7/1995 |
| EP | 1 3 83 448 B1 | 6/2008 |
| FR | 2 768 324 A1 | 3/1999 |
| FR | 2 768 325 B1 | 11/1999 |
| JP | H06128569 A | 5/1994 |
| JP | H0872058 A | 3/1996 |
| JP | H08334221 A | 12/1996 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | 9640354 | 12/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | 2006116558 | 11/2006 |
| WO | WO 2015/057289 A1 | 4/2015 |
| WO | 2016064748 | 4/2016 |
| WO | 2016183485 | 11/2016 |
| WO | WO 2016/178722 A1 | 11/2016 |
| WO | 2017003802 A1 | 1/2017 |
| WO | WO 2017/151566 A1 | 9/2017 |
| WO | WO 2018/093663 A1 | 5/2018 |
| WO | WO 2018/143560 A1 | 8/2018 |

OTHER PUBLICATIONS

U.S. Appl. No. 17/096,684, filed Nov. 12, 2020.
Hahn et al., Accurate Measurement of Left Ventricular Outflow Tract Diameter Comment on the Updated Recommendations for the Echocardiographic Assessment of Aortic Valve Stenosis, Journal of the American Society of Echocardiography 30(10):1038-1041 (2017).
Jianjun Dai et al., "Biomass feeding for thermochemical reactor", Progress in Energy and Combustion Science, 38, (2012) 716-736.

* cited by examiner

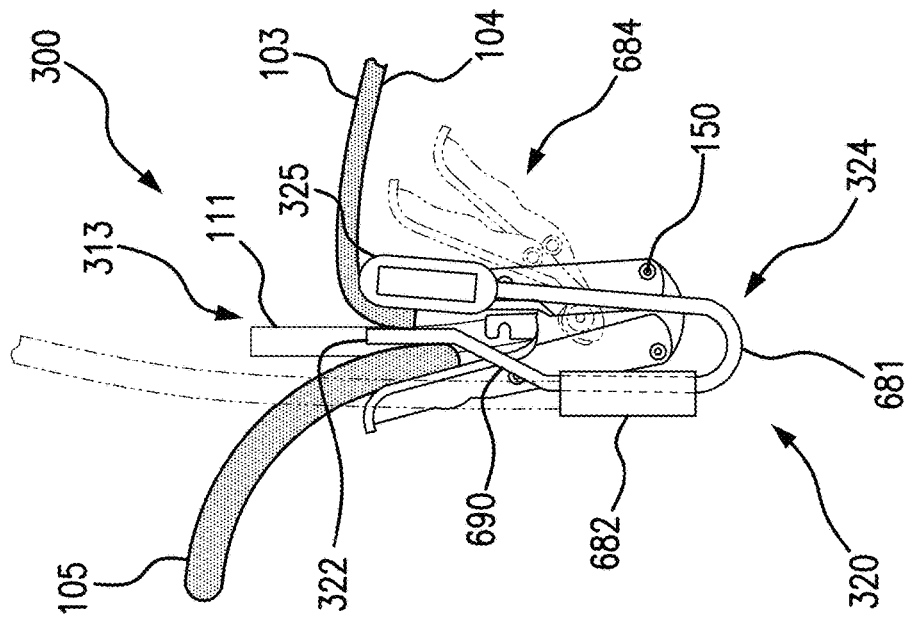
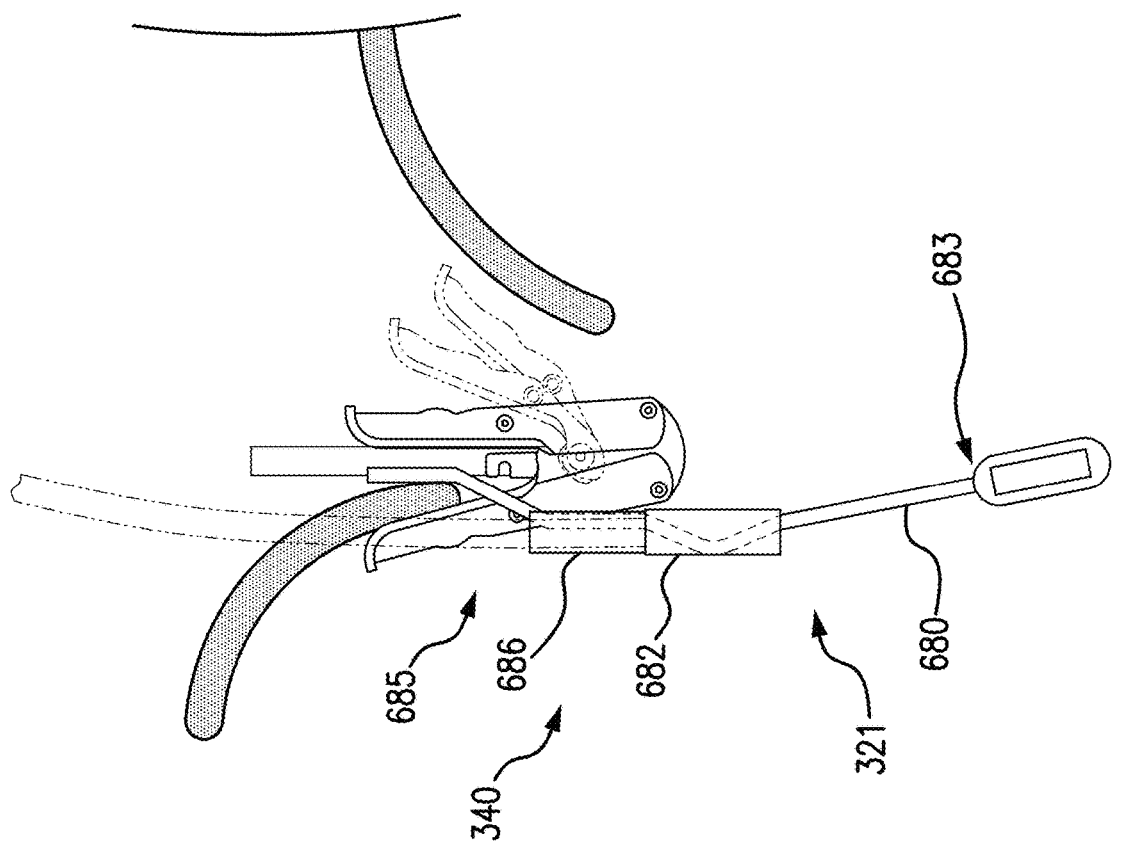

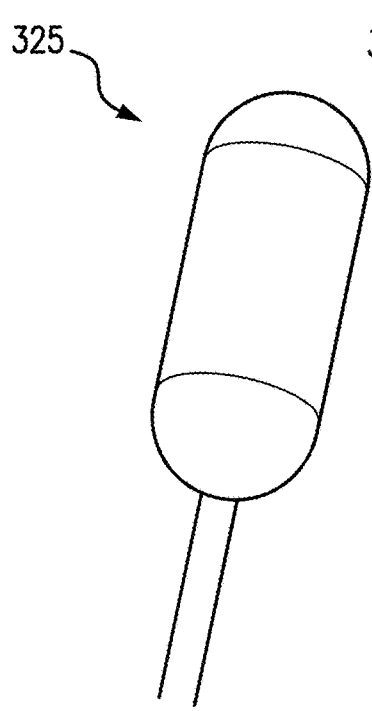 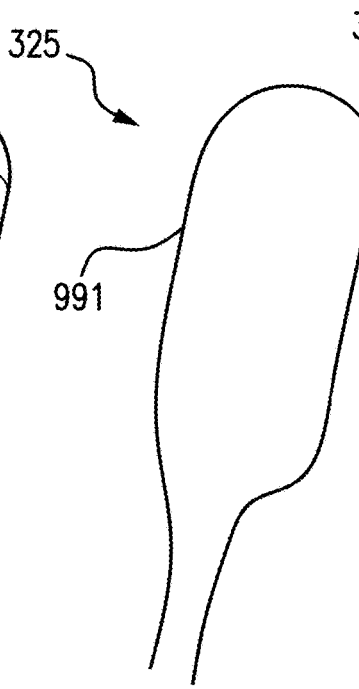 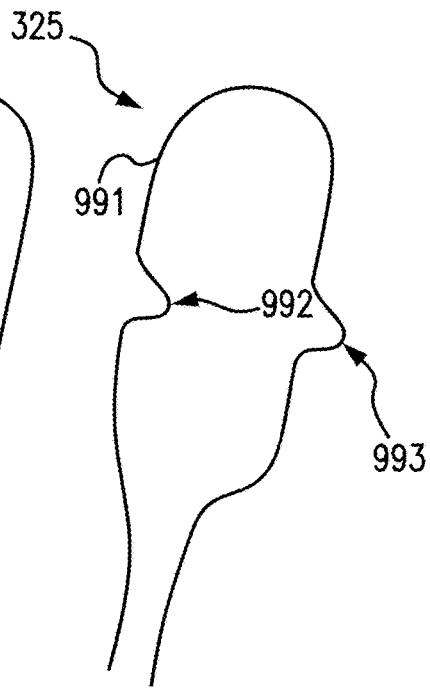
FIG. 9A   FIG. 9B   FIG. 9C
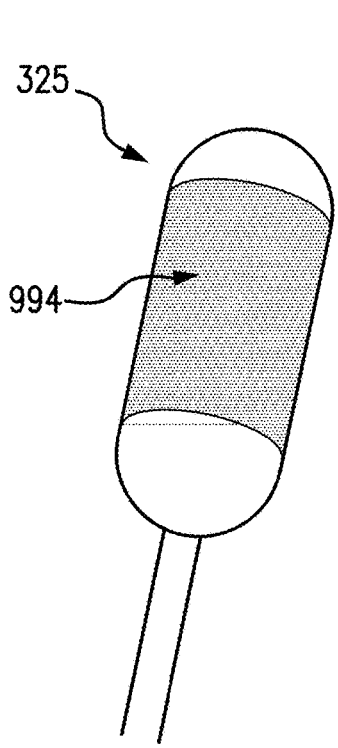 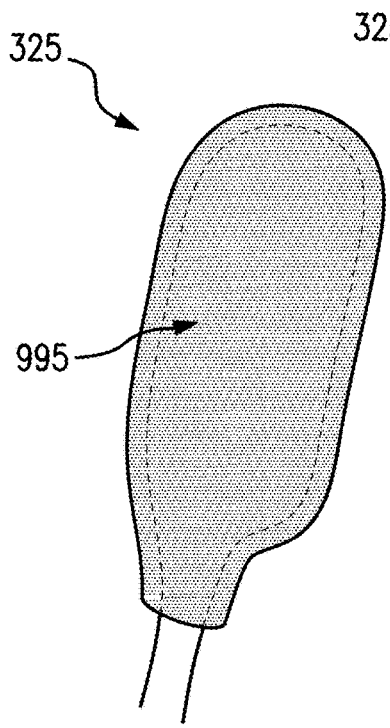 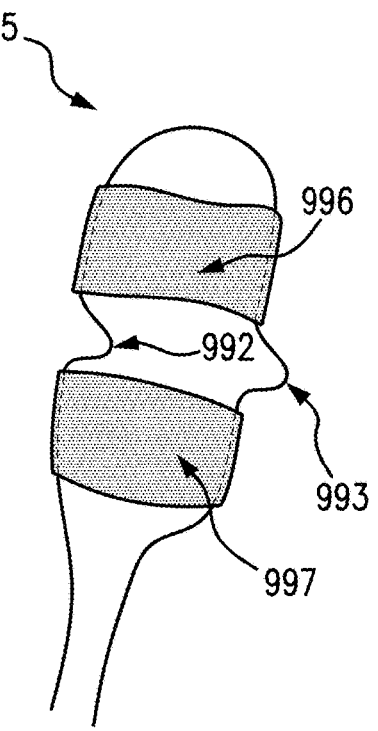
FIG. 9D   FIG. 9E   FIG. 9F ial Appli-
CATHETER ASSEMBLY WITH COAPTATION AID AND METHODS FOR VALVE REPAIR

CROSS-REFERENCE TO RELATED APPLICATIONS

This application claims priority to U.S. Provisional Application No. 62/935,227, filed Nov. 14, 2019, the full disclosure of which is incorporated herein by reference in its entirety.

FIELD OF DISCLOSED SUBJECT MATTER

The disclosed subject matter is directed to medical devices and methods for the endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement, which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae, which connect the leaflets to the papillary muscles, the papillary muscles or the left ventricular wall can be damaged or otherwise dysfunctional. Commonly, the valve annulus can be damaged, dilated, or weakened, limiting the ability of the mitral valve to close adequately against the high pressures of the left ventricle. In some anatomies, the anterior mitral leaflet can be positioned at a significant distance away from the opposing posterior mitral leaflet or the anterior leaflet can dynamically move away from the region of coaptation with the posterior leaflet, and there is a need for repair assemblies enabling leaflet grasping in such or similar anatomies.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a catheter assembly with a coaptation aid for repair of leaflets of a heart valve. The catheter assembly includes an elongate catheter shaft having a proximal portion and a distal portion adapted to be positioned transvascularly proximate a heart valve. The catheter assembly includes a lever coupled to the distal portion of the catheter shaft, the lever having a proximal end, a distal end, and a hinge to transition the lever between an elongate delivery configuration generally aligned longitudinally with the distal portion of the catheter shaft and a deployed configuration extending transversely from the distal portion of the catheter shaft. The lever also has an atraumatic tip proximate the distal end thereof adapted to contact a distal side of a native leaflet of the heart valve when the distal portion of the catheter shaft is positioned proximate the heart valve and the lever is in the deployed configuration. The catheter assembly also includes an actuation assembly coupled to the lever to remotely transition the lever between the delivery configuration and the deployed configuration.

The actuation assembly can include a transmission member extending along a length of the catheter shaft to remotely transition the lever between the delivery configuration and the deployed configuration. The transmission member can include a pull wire to transition the lever from the delivery configuration to the deployed configuration by rotating the lever about the hinge. The lever can be biased toward the delivery configuration. The pull wire can extend through an alignment loop disposed on the distal portion of the catheter shaft. The pull wire can extend through a lumen along a length of the catheter shaft. The actuation assembly can further include a linkage coupled to the lever with the pull wire attached to the linkage. The linkage can be coupled to the lever between the hinge and the distal end.

The atraumatic tip can comprise rounded edges and can comprise one or more of nitinol, cobalt chromium, stainless steel, titanium, polyether block amide (PEBAX), polylactic acid (PLA), poly-l-lactide (PLLA), polylactic-co-glycolic acid (PLGA), polyurethane, polyethylene, polyester, and polyamide.

The catheter assembly can further include a second lever coupled to the distal portion of the catheter shaft, the second lever having a proximal end, a distal end, and a hinge to transition the second lever between the delivery configuration and the deployed configuration. The second lever can further include a second atraumatic tip proximate the distal end of the second lever adapted to contact the distal side of the native leaflet. The actuation assembly can include a transmission member extending along a length of the catheter shaft to remotely transition the lever and the second lever simultaneously between the delivery configuration and the deployed configuration. The transmission member can include a pull wire attached to a linkage coupled to both the lever and the second lever to simultaneously transition the lever and the second lever from the delivery configuration to the deployed configuration by rotating each lever about its hinge. The pull wire can extend through an alignment loop disposed on the distal portion of the catheter shaft. The pull wire can extend through a lumen along a length of the catheter shaft.

The hinge can be defined as a preset bend in the lever. The actuation assembly can include a slidable collar disposed on the lever. The collar can be slidable between a delivery condition positioned over the hinge to straighten the bend of the lever to the delivery configuration and a deployed condition with the bend exposed to allow the lever to transition to the deployed configuration. The lever can be made of a super elastic material. The actuation assembly can include a transmission member, which can be a rod adapted to slide the collar between the delivery condition and the deployed condition. The rod can be a hypotube.

The lever can include a varied mechanical property along a length thereof. The varied mechanical property can be selected from a varied thickness or a varied material property. The varied mechanical property can include a stiffening member along a length thereof.

The lever can be made of a material selected from the group consisting of a metal, a polymer, a composite, or a combination thereof. The lever can include a wire.

The catheter assembly can further include a leaflet fixation device releasably coupled to the distal portion of the catheter shaft. The leaflet fixation device can include a first gripper assembly and a second gripper assembly, each gripper assembly configured to capture a respective native leaflet.

In accordance with the disclosed subject matter, a method for fixation of native leaflets of a heart valve includes introducing a catheter assembly transvascularly, the catheter assembly having an elongate catheter shaft with a proximal portion and a distal portion. The catheter assembly also includes a lever coupled to the distal portion of the catheter shaft. The lever has a proximal end, a distal end, and a hinge to transition the lever between an elongate delivery configuration generally aligned longitudinally with the distal portion of the catheter shaft and a deployed configuration extending transversely from the distal portion of the catheter shaft. The lever also includes an atraumatic tip proximate the distal end thereof. The catheter assembly also includes an actuation assembly coupled to the lever to remotely transition the lever between the delivery configuration and the deployed configuration. The catheter assembly also includes a leaflet fixation device releasably coupled to the distal portion of the catheter shaft and including a first gripper assembly and a second gripper assembly. The method also includes positioning the catheter with the distal portion positioned proximate the heart valve and deploying the first gripper assembly to capture a first native leaflet, actuating the actuation assembly to remotely transition the lever from the delivery configuration toward the deployed configuration to position the atraumatic tip against the distal side of a second native leaflet, and deploying the second gripper assembly to capture the second native leaflet.

The method for fixation of native leaflets of a heart valve can include any of the features described above for the catheter assembly with a coaptation aid.

BRIEF DESCRIPTION OF THE FIGURES

FIGS. 6A and 6B are front views of another exemplary embodiment of a catheter assembly with coaptation aid for repair of leaflets of a heart valve having a slidable collar and illustrate a method for fixation of native leaflets of a heart valve in accordance with the disclosed subject matter.

FIGS. 9A, 9B, 9C, 9D, 9E and 9F are front views of various exemplary embodiments of an atraumatic tip for a coaptation aid for repair of leaflets of a heart valve in accordance with the disclosed subject matter.

DETAILED DESCRIPTION

Reference will now be made in detail to various exemplary embodiments of the disclosed subject matter, which are illustrated in the accompanying drawings. A technique for mitral valve repair, which relies on suturing adjacent segments of the opposed valve leaflets together is referred to as the "bow-tie" or "edge-to-edge" technique. The catheter assemblies and methods of the disclosed subject matter provide for repair of leaflets of a heart valve, such as edge-to-edge valve repair for patients having various conditions, such as a regurgitant mitral valve. Such assemblies and method likewise can be useful for repair of tissues in the body other than heart valves. The assemblies and methods disclosed herein do not require open chest access and are capable of being performed endovascularly, i.e., using devices, such as a catheter, which are advanced to the heart from a point in the patient's vasculature remote from the heart.

Figure 1A:
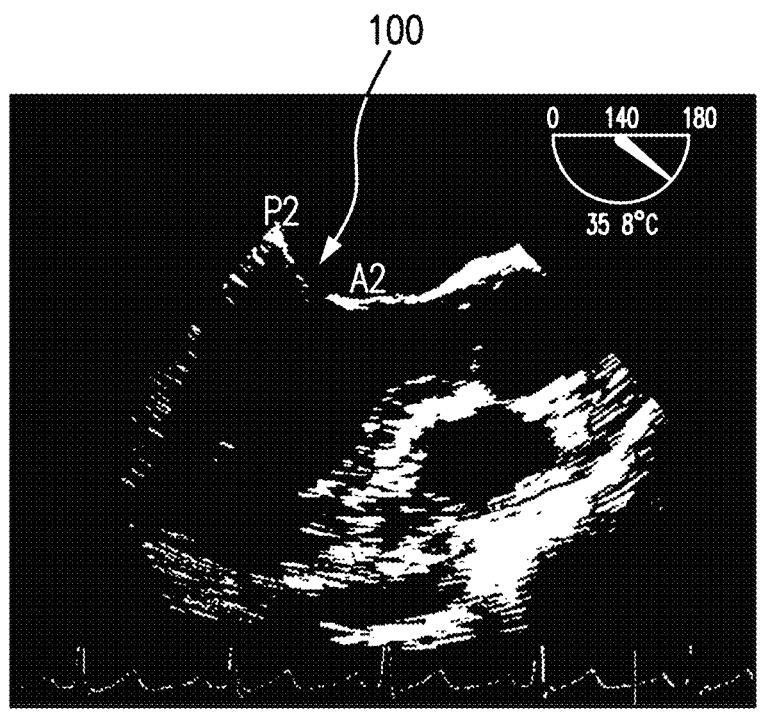
FIG. 1A is a trans-esophageal echocardiography image of a mitral valve.

For the purpose of illustration and not limitation, FIG. 1A is trans-esophageal echocardiography image of a heart valve 100, specifically a left ventricular outflow tract view of a mitral valve. Such a trans-esophageal echocardiography can be used for visualization during an edge-to-edge mitral valve repair procedure.

Figure 1B:
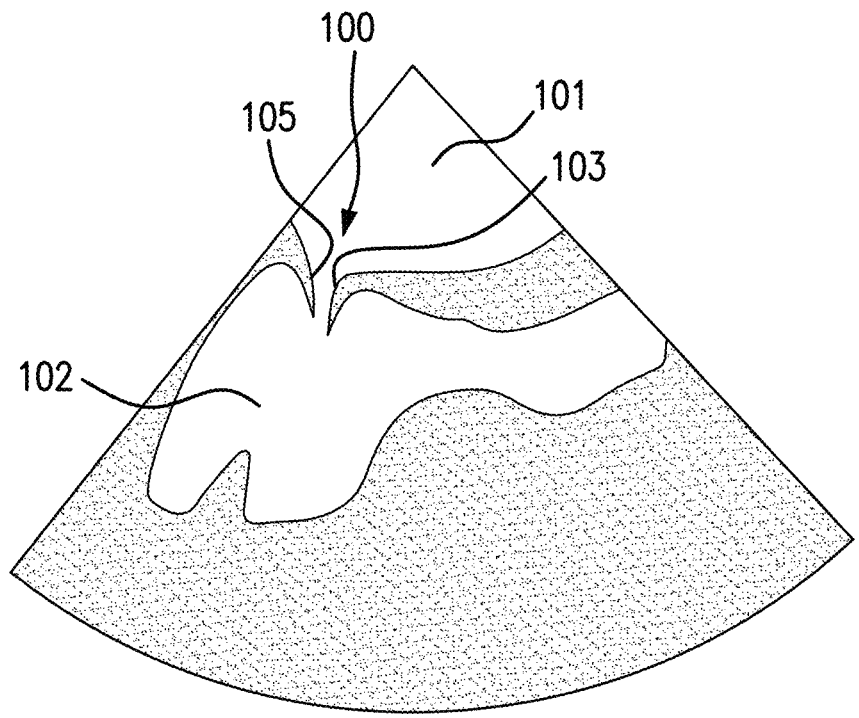
FIG. 1B is a schematic illustration of the mitral valve anatomy of FIG. 1A.

FIG. 1B is a schematic illustration of the mitral valve 100 of FIG. 1A and depicts the mitral anatomy including an anterior mitral leaflet 103 and a posterior mitral leaflet 105 that open and close to control blood flow from the left atrium 101 to the left ventricle 102 and further through the left ventricular outflow tract 106. FIG. 1B (and the trans-esophageal echocardiography of FIG. 1A) shows a mild regurgitation disease state, where the mid-sections of the anterior mitral leaflet 103 (A2 in FIG. 1A) and posterior mitral leaflet 105 (P2 in FIG. 1A) are shown to be non-coapting, but to be reasonably close to each other during cardiac systole. Edge-to-edge valve repair can be performed using a leaflet fixation device by targeting each leaflet to improve coaptation of the anterior and posterior mitral leaflets and reduce regurgitation.

Figure 1C:
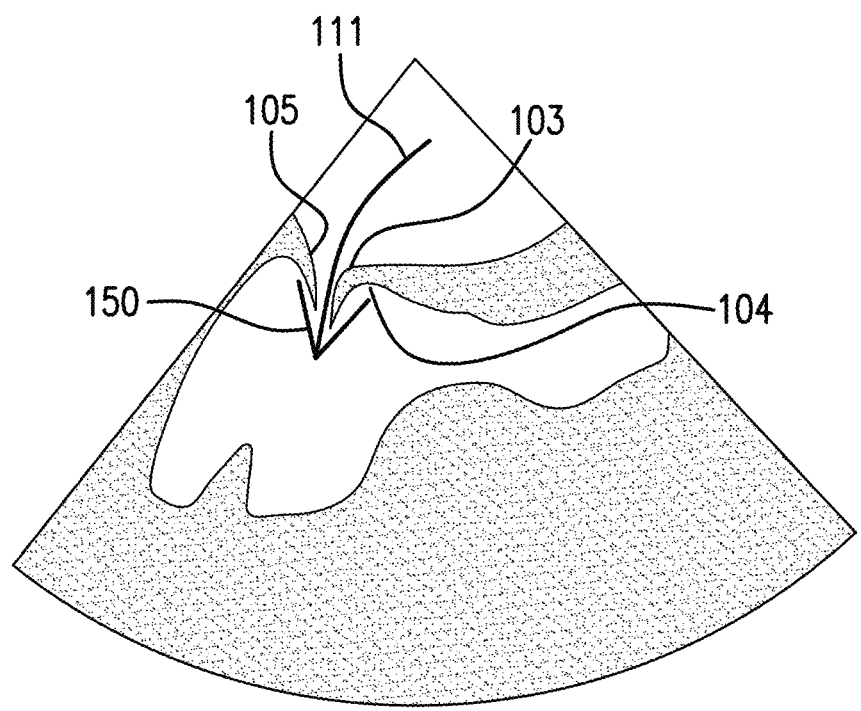
FIG. 1C is a schematic illustration of the mitral valve anatomy of FIG. 1A having a leaflet fixation device for edge-to-edge repair positioned to reach both leaflets of the mitral valve.

As illustrated in FIG. 1C, when performing transcatheter edge-to-edge repair, a leaflet fixation device 150 is delivered on the distal end of a catheter shaft 111 such that the opposing leaflets 103, 105 are inserted within a leaflet fixation device 150 and brought together into coaptation. These fixation devices can use arms to contact the distal side 104 of leaflets. Once the arms are positioned to stabilize the leaflets in a beating heart, gripping elements or the like contact the atrial side of the leaflets to capture the leaflets. Once both opposing leaflets are captured, the fixation device 150 can be closed such that the leaflets are pulled and brought into coaptation, which results in a reduction in valvular regurgitation during ventricular systole.

Figure 2A:
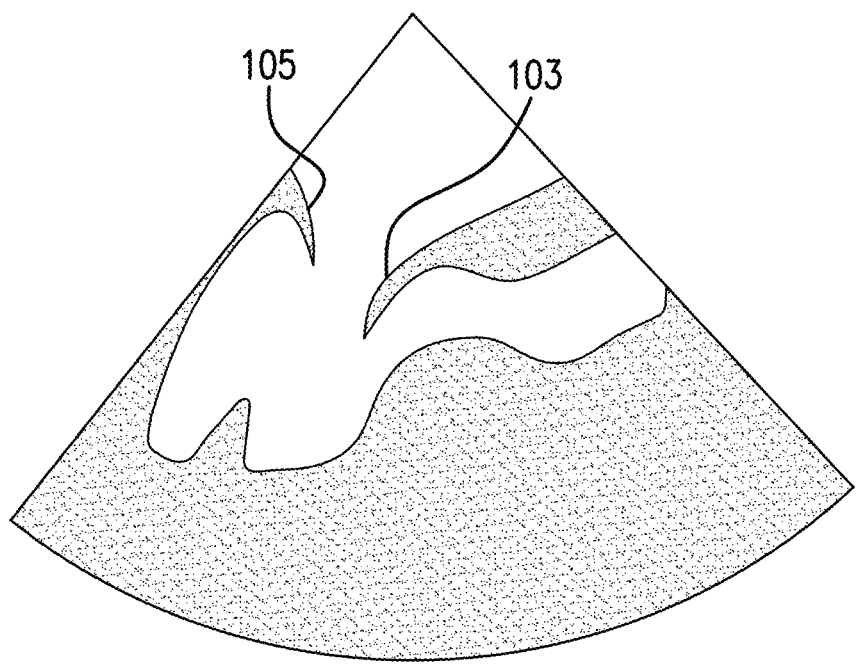
FIG. 2A is a schematic illustration of mitral valve anatomy having a depressed anterior mitral leaflet.
Figure 2B:
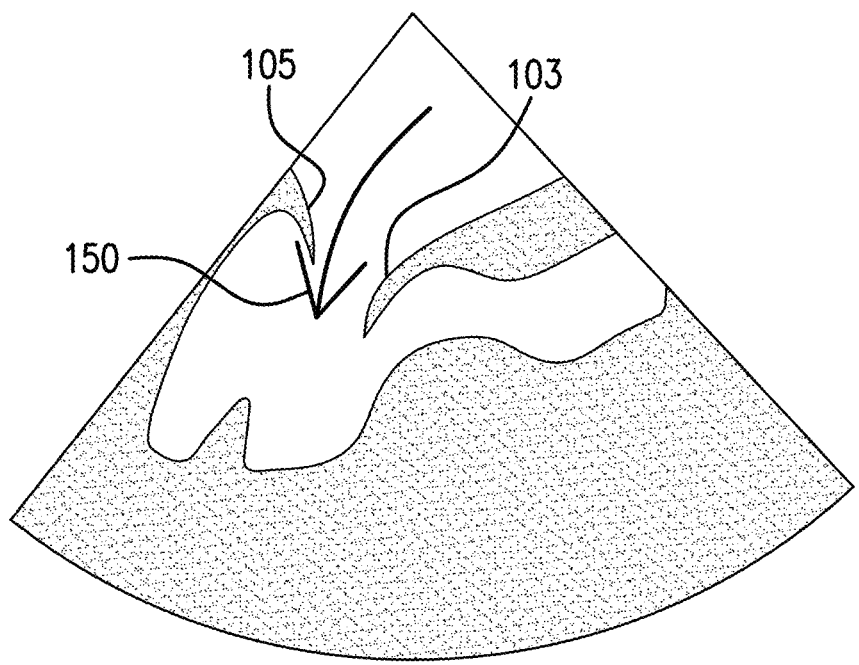
FIG. 2B is a schematic illustration of the mitral valve anatomy of FIG. 2A having a leaflet fixation device for edge-to-edge repair positioned proximate the posterior leaflet and not capable of reaching the anterior mitral leaflet.

However, leaflet locations can vary from patient to patient, and in certain patients it can be difficult to reach and capture both leaflets using fixation devices alone. For example, FIG. 2A depicts a mitral valve anatomy demonstrating a large coaptation gap, with the anterior mitral leaflet 103 depressed or spaced at a distance from the posterior mitral leaflet 105. As illustrated in FIG. 2B, because the anterior mitral leaflet 103 is significantly spaced from the posterior mitral leaflet 105, the leaflet fixation device 150 may not be able to reach the anterior mitral leaflet 103, and successful edge-to-edge repair may be difficult, requiring a great deal of procedural skill and time. The leaflet grasping procedure can be further complicated by erratic leaflet motion, such as systolic anterior motion of the anterior mitral valve leaflet. Further, if only a minimal amount of leaflet can be inserted within the arms and gripping elements during the procedure based upon the large gap, mitral regurgitation may not be significantly improved by a single implantation and additional devices or further intervention may be needed to reduce the mitral regurgitation.

To address these problems, generally, and as set forth in greater detail below, the disclosed subject matter includes a catheter assembly with a coaptation aid for repair of leaflets of a heart valve. The catheter assembly includes an elongate catheter shaft having a proximal portion and a distal portion adapted to be positioned transvascularly proximate a heart valve. The catheter assembly includes a lever coupled to the distal portion of the catheter shaft, the lever having a proximal end, a distal end, and a hinge to transition the lever between an elongate delivery configuration generally aligned longitudinally with the distal portion of the catheter shaft and a deployed configuration extending transversely from the distal portion of the catheter shaft. The lever also has an atraumatic tip proximate the distal end thereof adapted to contact a distal side of a native leaflet of the heart valve when the distal portion of the catheter shaft is positioned proximate the heart valve and the lever is in the deployed configuration. The catheter assembly also includes an actuation assembly coupled to the lever to remotely transition the lever between the delivery configuration and the deployed configuration.

Likewise, as further described in conjunction with the device of the disclosed subject matter, a method for fixation of native leaflets of a heart valve is provided. The method includes introducing a catheter assembly transvascularly, the catheter assembly having an elongate catheter shaft with a proximal portion and a distal portion. The catheter assembly also includes a lever coupled to the distal portion of the catheter shaft. The lever has a proximal end, a distal end, and a hinge to transition the lever between an elongate delivery configuration generally aligned longitudinally with the distal portion of the catheter shaft and a deployed configuration extending transversely from the distal portion of the catheter shaft. The lever also includes an atraumatic tip proximate the distal end thereof. The catheter assembly also includes an actuation assembly coupled to the lever to remotely transition the lever between the delivery configuration and the deployed configuration. The catheter assembly also includes a leaflet fixation device releasably coupled to the distal portion of the catheter shaft and including a first gripper assembly and a second gripper assembly. The method also includes positioning the catheter with the distal portion positioned proximate the heart valve and deploying the first gripper assembly to capture a first native leaflet, actuating the actuation assembly to remotely transition the lever from the delivery configuration toward the deployed configuration to position the atraumatic tip against the distal side of a second native leaflet, and deploying the second gripper assembly to capture the second native leaflet.

The coaptation aid thus can improve the ease of leaflet grasping and capture by providing a mechanism to temporarily facilitate positioning and stabilization of a leaflet, such as the anterior mitral leaflet, during an edge-to-edge repair procedure.

Figure 3A:
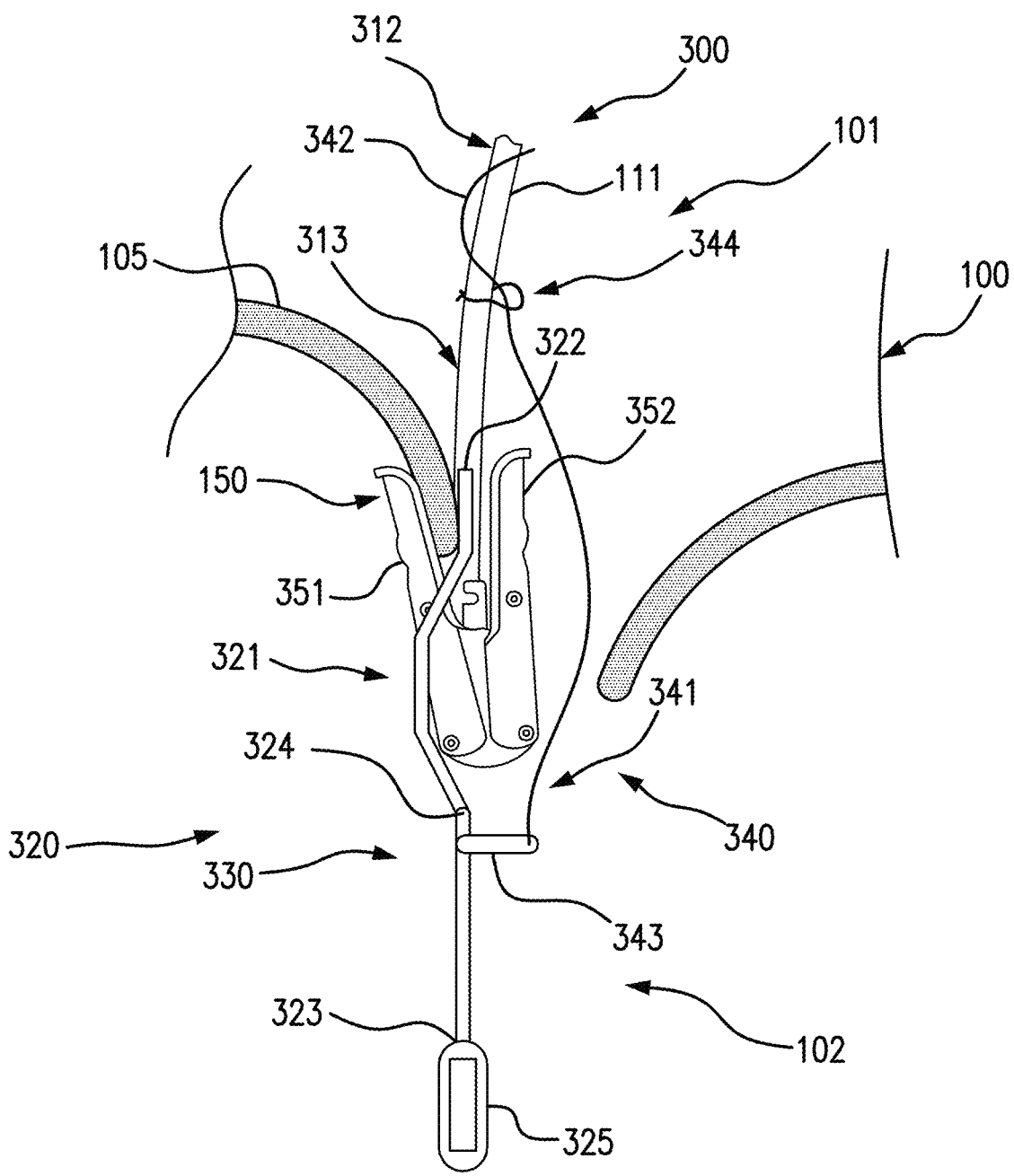
FIGS. 3A, 3B, and 3C are front views of an exemplary embodiment of a catheter assembly with a coaptation aid for repair of leaflets of a heart valve and illustrate a sequential schematic illustration of a method for fixation of native leaflets of a heart valve in accordance with the disclosed subject matter.

Referring to FIG. 3A, for purpose of illustration and not limitation, an exemplary catheter assembly 300 includes an elongate catheter shaft 111 having a proximal portion 312 and a distal portion 313. The catheter assembly 300 includes a coaptation aid 320 having a lever 321 coupled to the distal portion 313 of the catheter shaft. The lever 321 includes a proximal end 322, a distal end 323, and a hinge 324. An actuation assembly 340 is coupled to the lever 321 to remotely transition the lever. The lever 321 has an atraumatic tip 325 proximate the distal end 323 thereof. A leaflet fixation device 150, e.g., a clip, is releasably coupled to the distal portion 313 of the catheter shaft and is configured to grasp and couple two (or more) leaflets together. Although a number of edge-to-edge leaflet repair devices are known, for purpose of understanding and not limitation, reference will be made herein to a fixation device having a first gripper assembly 351 and a second gripper assembly 352 to capture the native leaflets, wherein each gripper assembly includes a movable arm and gripper element to capture a native leaflet therebetween.

In use, the catheter assembly 300 is introduced proximate the native leaflets of a heart valve 100, for example using an antegrade approach from a patient's left atrium 101 to the left ventricle 102. In a transcatheter approach, the catheter assembly 300 can be introduced in a femoral vein and advanced through the inferior vena cava into the heart, across a penetration in the interatrial septum (i.e., a transseptal approach), and to the mitral valve from the atrium toward the ventricle. Details of various suitable approaches for leaflet repair are set forth, for example, in U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Pat. No. 7,635,329 to Goldfarb et al., U.S. Patent Application Publication No. 2017/0042546 to Goldfarb et al., U.S. Patent Application Publication No. 2017/0239048 to Goldfarb et al., U.S. Patent Application Publication No. 2018/0325671 to Abunassar et al., the contents of each of which is incorporated by reference in its entirety herein (collectively "the Representative Patent Publications").

Once located proximate native leaflets of a heart valve 100, the first gripper assembly 351 of the leaflet fixation device 150 is deployed to capture a first native leaflet, such as the posterior mitral leaflet 105, as depicted in FIG. 3A. For example, arms of the fixation device 150 can be aligned generally perpendicular to a line of coaptation of the mitral valve, with the device positioned so that a first arm contacts the ventricular surface of the posterior mitral leaflet 105. A corresponding gripping element can remain on the atrial side of the valve leaflet so that the leaflet lies between the gripping element and the arm. As embodied herein, the first gripping element can be lowered toward the arm so that the leaflet is captured and held therebetween. Alternatively, the leaflet can be held with the arm underneath without lowering the gripping element until later in the procedure. Additional features and alternative embodiments of leaflet fixation devices and the grasping and capture process are described in more detail in the Representative Patent Publications.

In certain anatomies where the anterior mitral leaflet is significantly spaced from the posterior mitral leaflet or has dynamically moved away from the region of coaptation where edge-to-edge repair using the leaflet fixation device would not be possible, the coaptation aid of the disclosed subject matter can be used to position the anterior mitral leaflet close to the posterior mitral leaflet to allow for edge-to-edge repair.

Figure 3B:
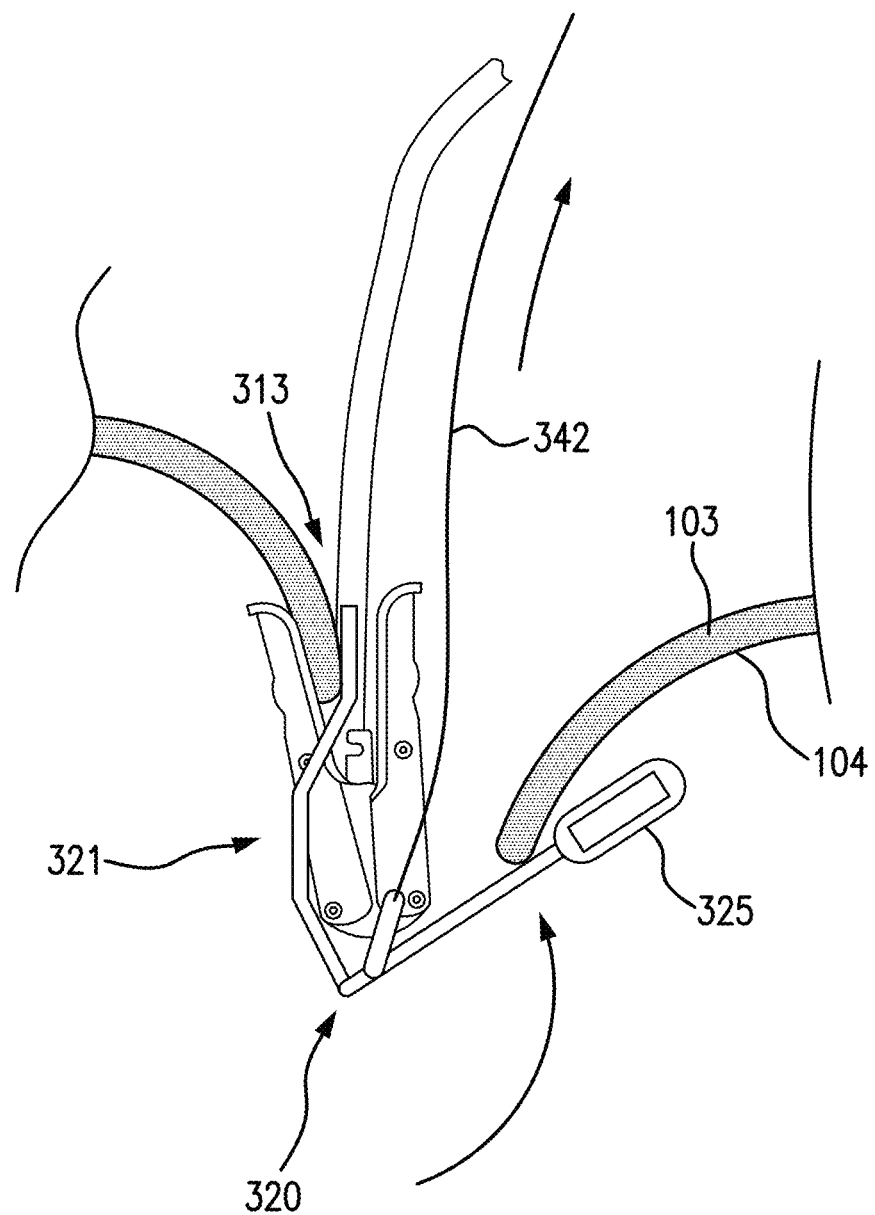

For example, lever 321 of the coaptation aid 320 is transitioned to locate the atraumatic tip 325 on the distal side 104 of the leaflet as shown in FIG. 3B and described in more detail below. The lever 321 can be made of a material selected from the group consisting of a metal, a polymer, a composite, or a combination thereof. For example, the lever 321 can include a wire. The tip 325 can be configured to be atraumatic, e.g., by using a suitable construction (as further detailed herein below) such as a flexible polymeric solid or hollow component, a flexible nitinol mesh component, or a flexible metallic component. A metallic version of the tip can be coated or jacketed with polymeric material such as PEBAX. Exemplary materials that can be used for the atraumatic tip include any combination of nitinol, cobalt chromium, stainless steel, titanium, polyether block amide (PEBAX), polylactic acid (PLA), poly-l-lactide (PLLA), polylactic-co-glycolic acid (PLGA), polyurethane, polyethylene, polyester, polyamide, and other suitable materials. The tip 325 can also be configured to be atraumatic, e.g., by using rounded edges and/or a tapered configuration, to reduce damage to the leaflets, chordae tendinae, papillary muscles, ventricular wall, and other heart tissue. Additionally, the atraumatic tip 325 should be dimensioned sufficiently slender to reduce entanglement with subvalvular structures including the papillary muscles and/or chordae tendinae when navigating through these structures.

With continued reference to FIG. 3A, the lever 321 has elongate configuration 330 during delivery to the heart valve 100, in which the lever is generally aligned longitudinally with and extends beyond the distal portion 313 of the catheter shaft to minimize profile and the bending stiffness of the catheter system. As embodied herein, the lever 321 is transitioned from the delivery configuration 330 via rotation about hinge 324 such that atraumatic tip 325 navigates through chordae tendinae and contacts a distal side 104 of the leaflet and begins to push the anterior leaflet 103 inward, as shown in a partially rotated configuration shown in FIG. 3B.

Figure 3C:
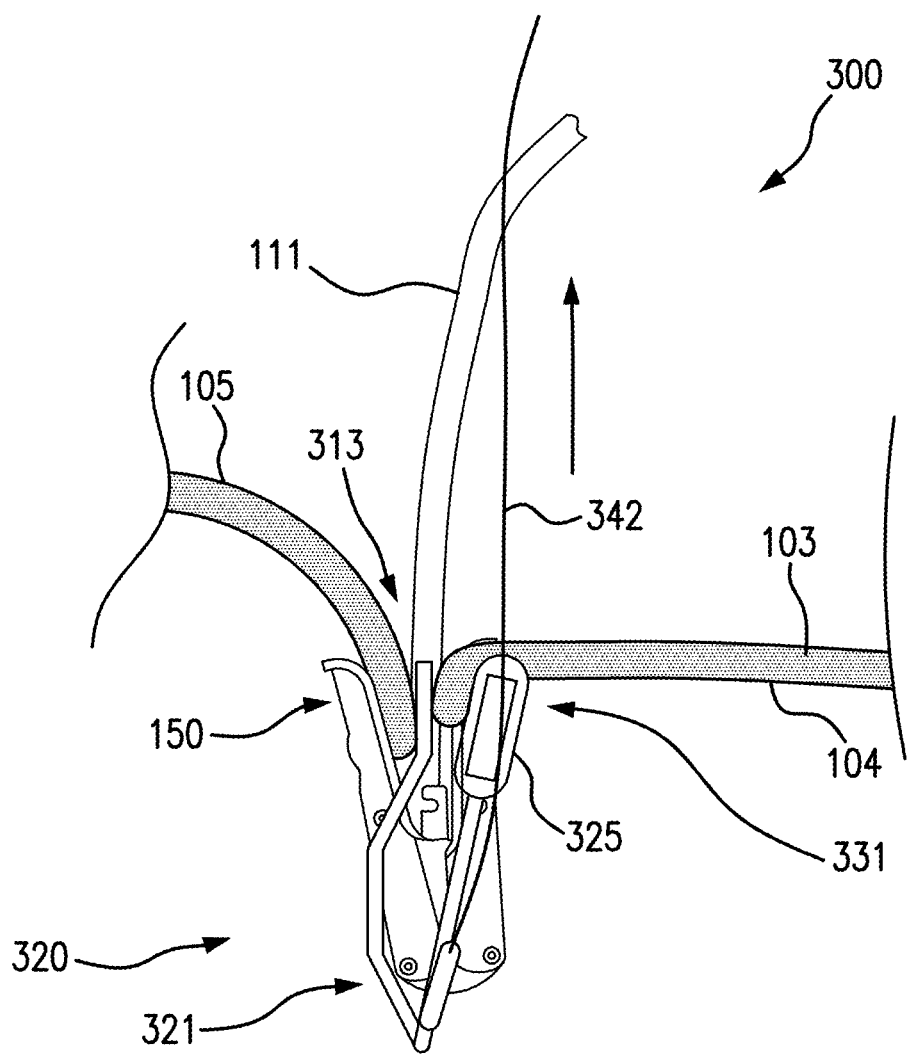

For example, and in accordance with the disclosed subject matter, in order to transition the lever 321 between the delivery configuration 330, as depicted schematically in FIG. 3A, and the deployed configuration 331, as depicted schematically in FIG. 3C, the catheter assembly 300 can include an actuation assembly 340 coupled to the lever 321. The actuation assembly 340 can include a transmission member 341, such as a wire, suture, or any suitable means, extending along a length of the catheter shaft 111. For example, the transmission member 341 can include a pull wire 342. The pull wire can extend through an alignment loop 344 disposed on the distal portion 313 of the catheter shaft to help guide the pull wire 342 toward a proximal portion (e.g., handle) of the catheter assembly (not shown) and reduce the chance of engagement with the catheter assembly 300 or cardiac structures. Additionally or alternatively, the pull wire can extend through a lumen along a length of the catheter shaft. Additional features and alternative embodiments of suitable catheter assemblies (including details of the proximal portion) are described in more detail in the Representative Patent Publications.

As embodied herein, the lever 321 can be biased toward the delivery configuration 330 and can be transitioned by applying tension to the pull wire 342 to transition the lever 321 from the delivery configuration 330 (FIG. 3A) to the deployed configuration 331 (FIG. 3C) by rotating the lever about the hinge 324 to position the atraumatic tip 325 against the distal side 104 of the native leaflet.

As embodied herein, with reference again to FIG. 3A, the actuation assembly 340 can further include a linkage 343 coupled to the lever 321. The linkage can include a wire rotatably connected to the lever 321 via a rivet or other suitable connecting means proximate a first end. The pull wire 342 can be attached to the linkage 343 proximate a second end. The linkage can be coupled to the lever 321 between the hinge 324 and the distal end 323 of the lever at a pivot distance to form a fulcrum and enable rotation of the lever about the hinge point.

The force applied to the leaflet to pull it into coaptation is proportional to the tension applied on the pull wire 342 and depends on the distance between the linkage 343 attachment location and the hinge 324 point and the distance between the atraumatic tip 325 and the hinge 324 point. Suitable distances between the linkage 343 attachment location and the hinge 324 point is about 5-10 mm and between the atraumatic tip 325 and the hinge 324 point is about 15-20 mm. In use, the coaptation load should not exceed about 0.8 to 1.0 lbf for an extended amount of time to reduce damage to leaflets and other cardiac tissue. Thus, the lever 321 can be adapted to apply a force of less than about 1.0 lbf to the native leaflet when the lever 321 is transitioned to the deployed configuration 331. The geometry shown in FIGS. 3A, 3B and 3C is exemplary, and one of ordinary skill in the art will recognize that any relative linkage attachment location, hinge point, curvature, damper or break in the hinge, variable thickness features, or stiffening features may be adjusted or additionally used to ensure loads do not impart excessive stress on the leaflets or the coaptation aid structure or its attachments.

For purpose of illustration, FIG. 3B depicts a modest amount of pull wire 342 tension being applied, which rotates the coaptation aid 320 such that the atraumatic tip 325 is brought into contact with the distal side 104 of the anterior leaflet 103. FIG. 3C shows the effect of further tension being applied on the pull wire 342, which swings the lever 321 and atraumatic tip 325 upward until a fully deployed configuration 331 is achieved. This rotation applies tension to the anterior leaflet 103 to bring it into a position located sufficiently close to the posterior leaflet 105 such that both leaflets can be grasped and captured by arms of the leaflet fixation device 150. In some anatomies, as depicted in FIG. 3B, in the deployed configuration 331, the lever 321 extends generally transversely from the distal portion 313 of the catheter shaft. Alternatively, in some anatomies, the lever 321 can fully rotate and extend generally aligned longitudinally with the distal portion 313 of the catheter shaft as depicted in FIG. 3C.

In the deployed configuration 331 of FIG. 3C, with the coaptation aid 320 acting as a stabilizing support for the anterior mitral leaflet 103, the fixation device 150 can be more easily used to simultaneously grasp both leaflets. The arm of the second gripper assembly 352 of the leaflet fixation device 150 is deployed to contact the ventricular surface 104 of and grasp the anterior mitral leaflet 103. The corresponding gripping element can remain on the atrial side of the leaflet so that the leaflet lies between the gripping element and the arm.

If needed, before the second gripper is deployed, the fixation device 150 can be repeatedly manipulated to reposition the device so that the leaflets are properly grasped at a desired location. Repositioning can be achieved with the fixation device 150 in an open position. For example, the coaptation aid 320 can be manipulated to reposition the leaflets, such as by applying additional tension or reducing tension on the pull wire 342 to better position the anterior mitral leaflet 103. As embodied herein, the catheter shaft 111 and or lever 321 of the coaptation aid can be longitudinally rotated to apply different tension on the leaflet via the atraumatic tip 325 to better position the leaflet for capture. Regurgitation of the valve can also be checked while the fixation device 150 is in the open position. If regurgitation is not satisfactorily reduced, the fixation device 150 can be repositioned, and regurgitation checked again until desired results are achieved.

Once the fixation device 150 has been positioned in a desired location relative to the valve leaflets, the leaflets can then be captured between the gripping elements and the arms. As noted above, the first gripping element may already have been lowered to capture the posterior leaflet. If so, the second gripping element is lowered to capture the anterior leaflet. Alternatively, if the posterior leaflet has not yet been captured, both gripping elements can be lowered toward the arms so that the leaflets are held and captured therebetween, either simultaneously or sequentially. Once both leaflets are captured, the arms can be closed to a tight arm angle to bring each leaflet into central coaptation to reduce regurgitation. The arms can further be locked to the prevent the device from moving toward an open position.

Once completed, the coaptation aid 320 can be removed by releasing tension on the pull wire 342. As tension is released, the coaptation aid 320 will not have any bending stiffness and will align with the delivery catheter for safe withdrawal from the body. The repair of the leaflets or tissue can be observed by non-invasive visualization techniques, such as echocardiography, to ensure the desired outcome. If the repair is not desired, the fixation device 150 can be repositioned or retrieved. Once the desired outcome is achieved, the fixation device 150 can be detached from the distal portion 313 of the catheter shaft, and the catheter assembly 300 with the coaptation aid 320 can be withdrawn from the body.

Figure 4A:
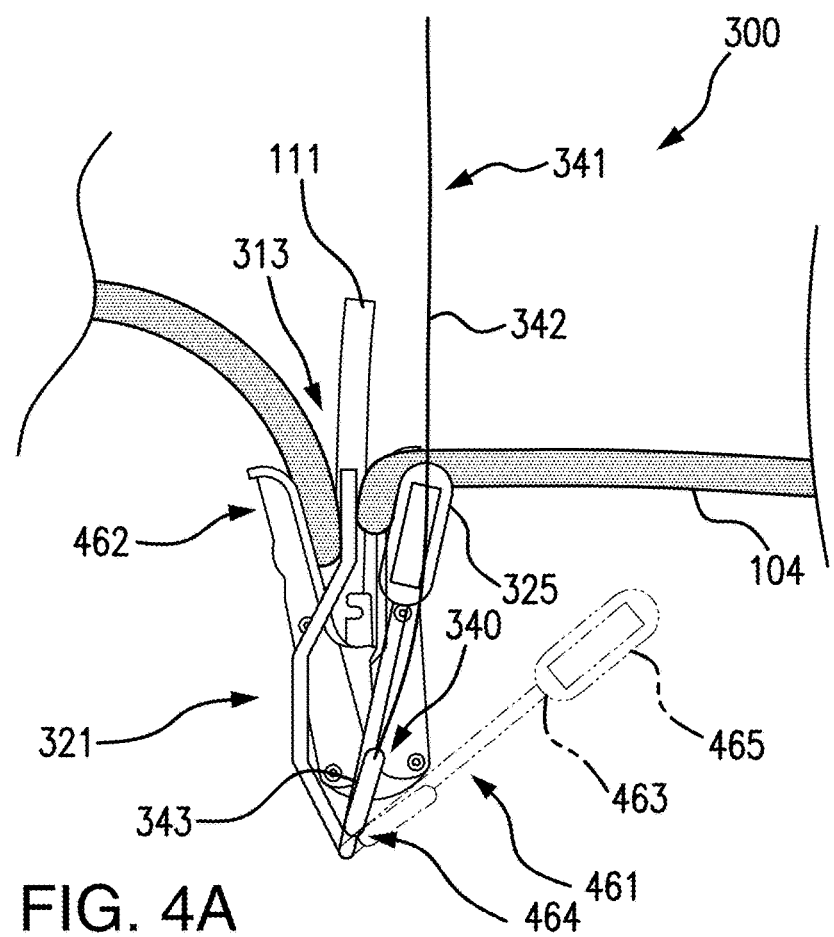
FIGS. 4A and 4B are front views of another exemplary embodiment of a catheter assembly with coaptation aid for repair of leaflets of a heart valve having two levers in accordance with the disclosed subject matter.
Figure 4B:
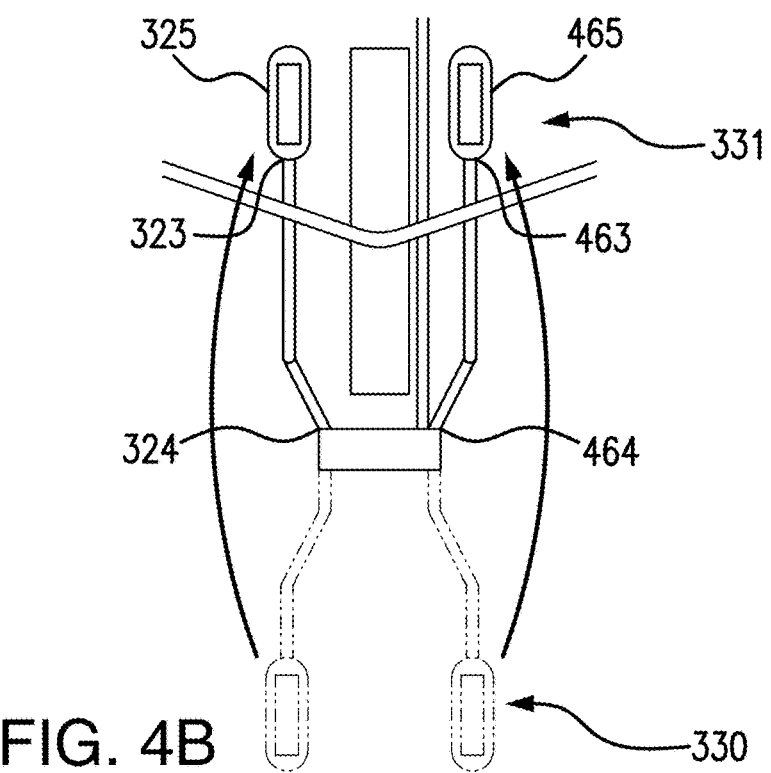

In accordance with another aspect of the disclosed subject matter, referring now to FIGS. 4A and 4B, the catheter assembly 300 can further include a second lever 461 coupled to the distal portion 313 of the catheter shaft, the second lever having a proximal end 462, a distal end 463, and a hinge 464 to transition the second lever between the delivery configuration 330 and the deployed configuration 331. For example, the second lever 461 can be coupled to the catheter shaft 111 on a side opposite the first lever 321. The second lever 461 can also include a second atraumatic tip 465 proximate the distal end 463 thereof adapted to contact the distal side 104 of the native leaflet. The hinge 464 can be a common hinge mechanism so that the two separate atraumatic tips 325, 465, rotate about the common hinge.

In embodiments with two levers and with continued reference to FIG. 4A, the actuation assembly 340 can include a transmission member 341 extending along a length of the catheter shaft 111. The transmission member 341 can include a wire, suture, or other suitable means, to remotely transition the lever 321 and the second lever 461 simultaneously between the delivery configuration and the deployed configuration. For example, the transmission member 341 includes a pull wire 342 attached to a linkage 343 coupled to both the lever 321 and the second lever 461 to simultaneously transition the lever and the second lever from the delivery configuration to the deployed configuration by rotating each lever about its hinge to position each atraumatic tip 325, 465 against the distal side 104 of the native leaflet.

Figure 5:
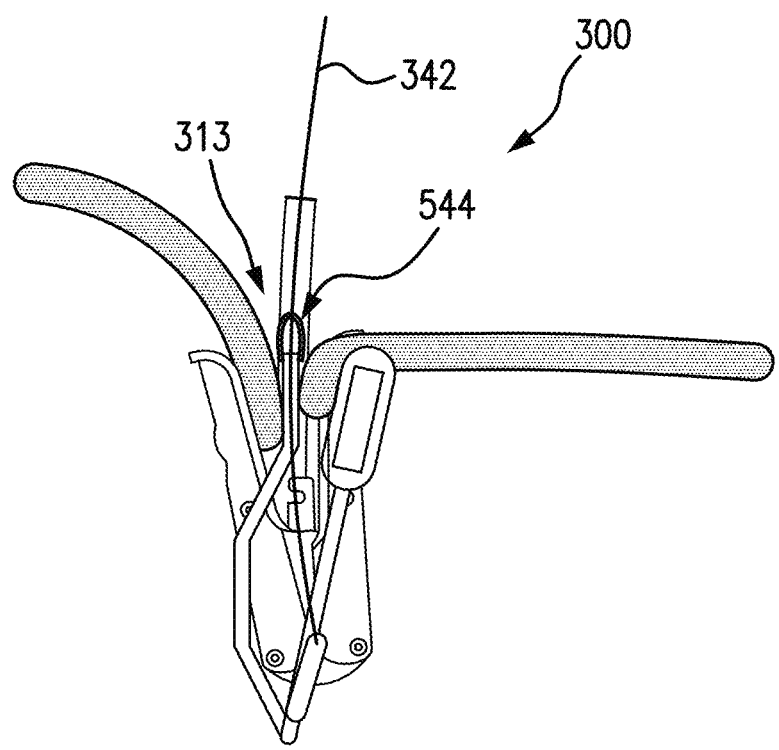
FIG. 5 is a front view of another exemplary embodiment of a catheter assembly with coaptation aid for repair of leaflets of a heart valve having an alignment loop in accordance with the disclosed subject matter.

With reference now to FIG. 5, as embodied herein, the pull wire 342 can extend through an alignment loop 544 disposed on the distal portion 313 of the catheter shaft. The alignment loop 544 can be a coaxial tether loop in order to route any pull wire 342 slack along a central axis of the catheter assembly 300 toward a proximal portion (e.g., handle) of the catheter assembly (not shown). The alignment loop 544 can be any suitable configuration to reduce entanglement or inference with the fixation device arms closing together on opposing leaflets. Additionally or alternatively, the pull wire can extend through a lumen along a length of the catheter shaft.

Embodiments of the disclosed subject matter with two levers can be used for valve repair, for example in edge-to-edge repair, in the same manner as described herein above. As embodied herein, each of the two atraumatic tips 325, 465 can be positioned just adjacent to the fixation device arms at a width dimension between, such as 6 mm to 10 mm, so that the leaflet areas on either side of the fixation device arm are supported during the repair procedure. Thus, the location of these tips ensures that the closing of the fixation devices arms is not obstructed.

In accordance with another aspect of the disclosed subject matter, and with reference to FIGS. 6A and 6B for purpose of illustration and not limitation, the hinge 321 is defined as a preset bend 681 in the lever 321. The lever 321 can be made of a super elastic material, such as nitinol, which can bias the lever 321 toward the deployed condition 684. If constructed using nitinol, the lever with hinge 324 (at bend 681) can incur strains up to about 8%.

With continued reference to FIGS. 6A and 6B, the actuation assembly 340 can include a slidable collar 682 disposed on the lever 321. The slidable collar 682 can be formed of any suitable material, such as nitinol, Elgiloy, stainless steel, polyether block amide (PEBAX), silicone, or other metal or polymer. Metallic and polymeric combinations can also be incorporated to form the slidable collar in a braided tubular configuration. The slidable collar 682 can have a length spanning at least twice the hinge radius of curvature of the bend 681 with an overall length between 6 and 12 mm. Additional bends 681 can be incorporated to form a series to maintain the elasticity of the hinge 324 during a wider range of motion, as shown below in connection with FIGS. 8A and 8B. In the case of incorporating multiple bends 681, the slidable collar 682 can have a length that encompasses twice the hinge radius of curvature of all bends that are being straightened by the slidable collar. The actuation assembly 340 can also include a transmission member 685 having a rod, such as a hypotube, 686 adapted to slide the collar 682 between a delivery condition 683, positioned over the hinge 324 to straighten the bend 681 of the lever, to a deployed condition 684, with the bend 681 exposed. The collar 682 can be pushed or pulled through a transmission rod, such as a hypotube, 686 (i.e., catheter's hollowed elongate member), which acts to either position the collar 682 directly on the hinge 324 as shown in FIG. 6A for the delivery condition 683 or proximal to the hinge 324 to reveal and actuate the hinge as shown in FIG. 6B for the deployed condition 684.

In accordance with another aspect of the disclosed subject matter, the lever 321 can include a varied mechanical property along a length thereof selected from a varied thickness or a varied material property. For example, the lever 321 can include a stiffening member 690, an exemplary embodiment of which is depicted in FIG. 6B, along a length thereof or can have a doubled-up portion to provide a varied thickness. Additionally or alternatively, the lever 321 can include a varied austinite finish temperature along its length. The varied mechanical property can ensure the lever applies a force of less than about 1.0 lbf to the native leaflet when the lever is transitioned to the deployed configuration.

Embodiments of the disclosed subject matter with a slidable collar 682 can be used for valve repair, for example in edge-to-edge repair, in the same manner as described herein above. For example, in use, as the slidable collar 682 is moved proximally to expose the bend 681, which rotates the coaptation aid 320 such that the atraumatic tip 325 is brought into contact with the distal (ventricular) side 104 of the anterior leaflet 103. Further proximal movement of the slidable collar 682 further swings the lever 321 and atraumatic tip 325 upward until a fully deployed condition 684 is achieved. This rotation applies tension to the anterior leaflet 103 to bring it into a position located sufficiently close to the posterior leaflet 105 such that both leaflets can then be grasped and captured by arms of the leaflet fixation device 150. The hinge radius of curvature shown in FIG. 6B is exemplary and a more or less dramatic curvature can be used.

Once completed, the coaptation aid 320 can be removed by pushing collar 682 distally over the bend 681, which will restore the slender profile of the delivery catheter for withdrawal from the body. The repair of the leaflets or tissue can be observed by non-invasive visualization techniques, such as echocardiography, to ensure the desired outcome. If the repair is not desired, the fixation device 150 can be repositioned or retrieved. Once the desired outcome is achieved, the fixation device 150 can then be detached from the distal end of the catheter shaft 111 and the catheter assembly 300 with the coaptation aid 320 can be withdrawn from the body.

Figure 7A:
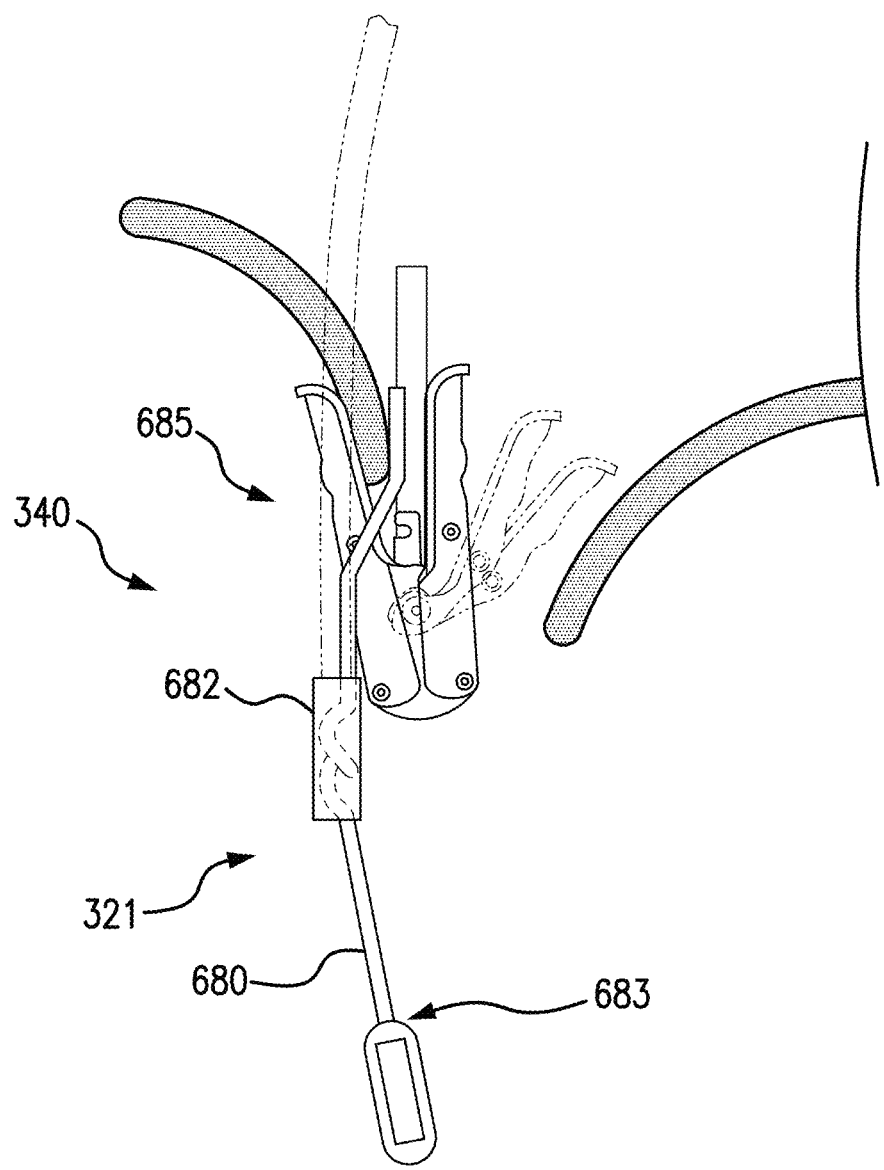
FIGS. 7A and 7B are front views of another exemplary embodiment of a catheter assembly with coaptation aid for repair of leaflets of a heart valve having a slidable collar in accordance with the disclosed subject matter.
Figure 7B:
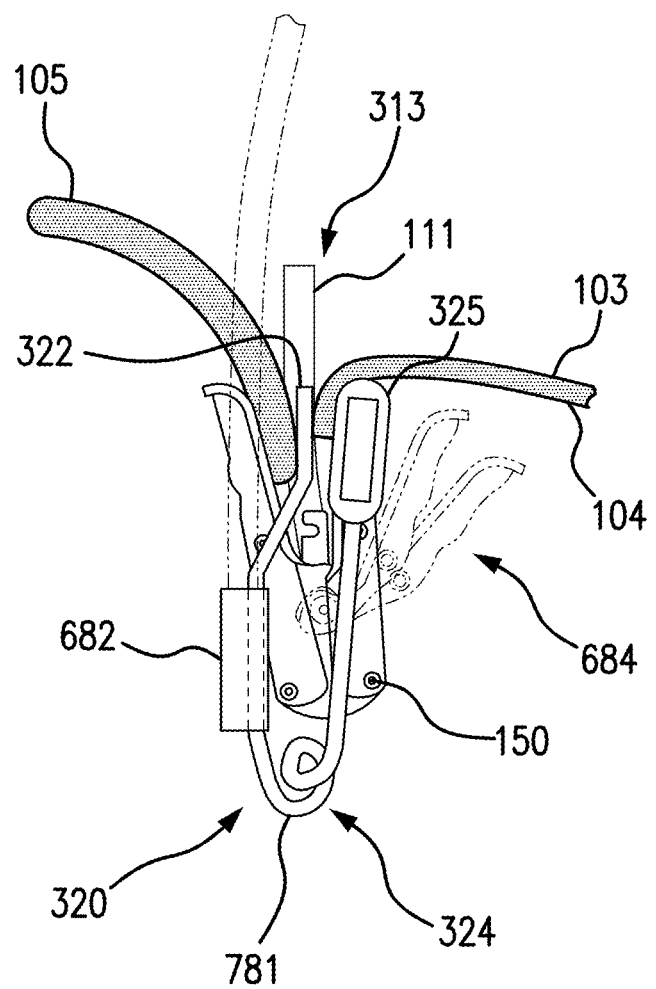

While a single bend 681 in lever 321 is illustrated in FIGS. 6A and 6B, the hinge 321 can have additional or alternative configurations. For example, as shown in FIGS. 7A and 7B, the bend 781 can include a coiled hinge. As shown in FIG. 7A, the coiled hinge 781 can be at least partially straightened and held under collar 682 in a delivery condition 683 during tracking and initial positioning prior to grasping the leaflets. As described above in connection with FIGS. 6A and 6B, slidable collar 682 can then be moved proximally to expose the hinge 781 as shown in FIG. 7B to move to a deployed condition 684 by activating the flexible coiled hinge and rotating the coaptation aid 320 such that the atraumatic tip 325 is brought into contact with the distal (ventricular) side 104 of the anterior leaflet 103. While a single coil loop 781 is illustrated in FIGS. 7A and 7B, additional loops can be used to distribute strain more evenly and still ensure an adequate range of motion of the coaptation aid without exceeding about 8 percent strain in the, e.g., nitinol structure. The coiled hinge 781 can be nitinol or another shape memory material, and in some embodiments the preset shape can be tuned to overshoot closure of the lever beyond parallel to ensure reliable force application occurs for a grasped leaflet.

Figure 8A:
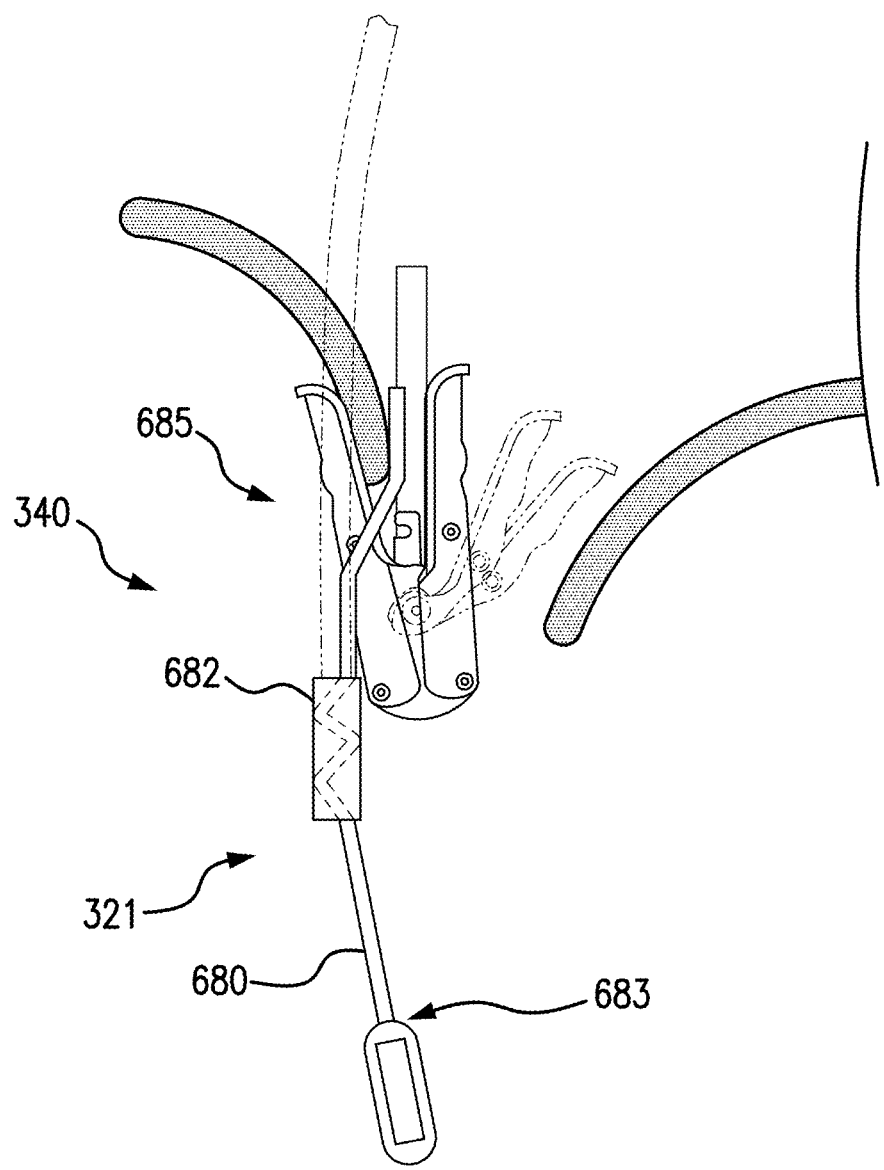
FIGS. 8A and 8B are front views of another exemplary embodiment of a catheter assembly with coaptation aid for repair of leaflets of a heart valve having a slidable collar in accordance with the disclosed subject matter.
Figure 8B:
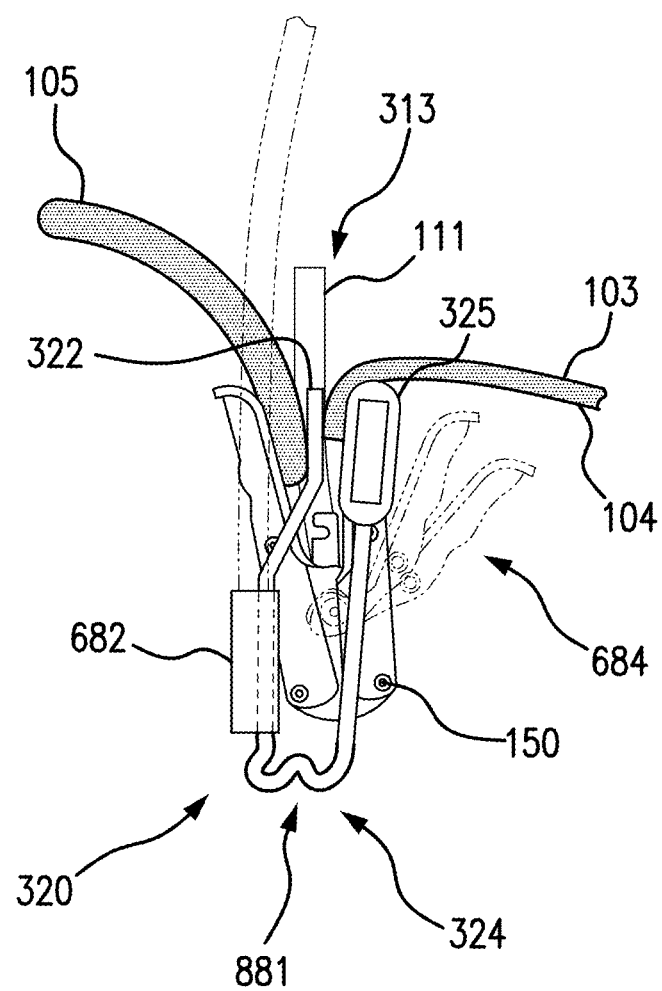

FIGS. 8A and 8B illustrate another exemplary embodiment of bend of lever 321 in which the bend 881 includes an series-style undulating hinge. As shown in FIG. 8A, the undulating hinge 881 can be at least partially straightened and held under collar 682 in a delivery condition 683 during tracking and initial positioning prior to grasping the leaflets. As described above in connection with FIGS. 6A and 6B, slidable collar 682 can then be moved proximally to expose the hinge 881 as shown in FIG. 8B to move to a deployed condition 684 by activating the flexible undulating hinge and rotating the coaptation aid 320 such that the atraumatic tip 325 is brought into contact with the distal (ventricular) side 104 of the anterior leaflet 103. While a double undulating hinge 881 is illustrated in FIGS. 8A and 8B, additional undulations can be used to distribute strain more evenly and still ensure an adequate range of motion of the coaptation aid without exceeding about 8 percent strain in the, e.g., nitinol structure. The undulating hinge 881 can be nitinol or another shape memory material, and in some embodiments the preset shape can be tuned to overshoot closure of the lever beyond parallel to ensure reliable force application occurs for a grasped leaflet.

The lever can have any suitable dimensions, for example including a diameter of 0.5 to 2 mm and have a length that approximately equals 0.75 to 1.25 times the length of the implant. The atraumatic tip can have any suitable shape including spherical, cylindrical, or any other shape with rounded edges and can have any suitable dimensions including a diameter and length of approximately 3-5 mm and 6-9 mm. The atraumatic tip may be a wire form, coil, or hollow braided structure that can gently deform or ovalize to conform to tissue contacted during use. In this way, stresses induced in the leaflets are minimized. For example, FIGS. 9A, 9B, 9C, 9D, 9E, and 9F illustrate various configurations for atraumatic tip 325. FIG. 9A shows a cylindrical molded atraumatic tip 325. FIG. 9B shows an atraumatic tip 325 formed from a wireform 991. In FIG. 9C, the wireform 991 further includes flexing hinges 992 and 993. FIG. 9D illustrates a cylindrical molded atraumatic tip 325 having a covering 994, e.g., formed of polyester, that can improve grip of the tip 325 on leaflets. FIG. 9E illustrates an atraumatic tip 325 formed from a wireform 991 having a covering 995, e.g., braided, that can that can improve grip of the tip 325 on leaflets. FIG. 9F illustrates an atraumatic tip 325 formed from a wireform 991 further includes flexing hinges 992 and 993, and having a two coverings 996 and 997, e.g., textile, that can that can improve grip of the tip 325 on leaflets. While certain coverings have been described in connection with certain atraumatic tip configurations, it is readily apparent that alternative combinations of coverings and tip configurations can also be used.

As embodied herein, coaptation aid 320 can be an optional accessory or permanently fixed to the catheter assembly 300. For example, the coaptation aid 320 can be part of a kit (not shown) including a catheter shaft 111 and a leaflet fixation device 150. Prior to a procedure, a user can observe the native anatomy and spacing between the leaflets to determine if a coaptation aid 320 will assist in the procedure. If so, the user can install or attach the coaptation aid 320 to the distal portion 313 of the catheter shaft of the delivery system. For example, the a proximal end 322 of a lever of the coaptation aid 320 can be removably connected to the distal portion 313 of the catheter shaft, e.g., by snap fit or the like. Alternatively, the coaptation aid 320 can run alongside the catheter shaft 111 of the delivery system without direct attachment thereto.

The embodiments illustrated herein are adapted for repair of a heart valve and have been described in connection with repair of a mitral valve, using an antegrade approach from a patient's left atrium. However, the disclosed subject matter can be used on any other leaflet that requires intraprocedural propping or positioning to make leaflet grasping and clipping easier. Other exemplary leaflets include, the posterior mitral leaflet, or any tricuspid, aortic, or pulmonary valve leaflet. Furthermore, while shown herein as a clip, the leaflet fixation device could be any suitable fixation means, including sutures, clips, staples, and the like. In addition, while a single device was shown and described in each embodiment herein, a plurality of devices or device features may be used to simultaneously support or stabilize two or more opposing leaflets in order to further simplify the edge-to-edge repair procedure. Further, while described in connection with an edge-to-edge repair procedure, the disclosure subject matter can be adapted to aid in other procedures, such as leaflet resection, minimally invasive leaflet suturing, and chordae replacement.

While the disclosed subject matter is described herein in terms of certain embodiments for purpose of illustration and not limitation, those skilled in the art will recognize that various modifications and improvements can be made to the disclosed subject matter without departing from the scope thereof. Moreover, although individual features of the disclosed subject matter may have been discussed herein or shown in the drawings of one embodiment and not in other embodiments, it is readily apparent that individual features of one embodiment can be combined with, or substituted for, one or more features of another embodiment or features from a plurality of embodiments.

In addition to the specific embodiments claimed below, the disclosed subject matter is also directed to other embodiments having any other possible combination of the dependent features disclosed above, claimed below, and listed below:

The actuation assembly can include a transmission member extending along a length of the catheter shaft to remotely transition the lever between the delivery configuration and the deployed configuration.

The transmission member can include a pull wire to transition the lever from the delivery configuration to the deployed configuration by rotating the lever about the hinge.

The lever can be biased toward the delivery configuration.

The pull wire can extend through an alignment loop disposed on the distal portion of the catheter shaft.

The pull wire can extend through a lumen along a length of the catheter shaft.

The actuation assembly can further include a linkage coupled to the lever with the pull wire attached to the linkage.

The linkage can be coupled to the lever between the hinge and the distal end.

The lever is adapted to apply a force of less than about 1.0 lbf to the native leaflet when the lever is transitioned to the deployed configuration.

The atraumatic tip can comprise rounded edges and can comprise one or more of nitinol, cobalt chromium, stainless steel, titanium, polyether block amide (PEBAX), polylactic acid (PLA), poly-l-lactide (PLLA), polylactic-co-glycolic acid (PLGA), polyurethane, polyethylene, polyester, and polyamide.

The catheter assembly can further include a second lever coupled to the distal portion of the catheter shaft, the second lever having a proximal end, a distal end, and a hinge to transition the second lever between the delivery configuration and the deployed configuration.

The second lever can further include a second atraumatic tip proximate the distal end of the second lever adapted to contact the distal side of the native leaflet.

The actuation assembly can include a transmission member extending along a length of the catheter shaft to remotely transition the lever and the second lever simultaneously between the delivery configuration and the deployed configuration.

The transmission member can include a pull wire attached to a linkage coupled to both the lever and the second lever to simultaneously transition the lever and the second lever from the delivery configuration to the deployed configuration by rotating each lever about its hinge.

The pull wire can extend through an alignment loop disposed on the distal portion of the catheter shaft.

The pull wire can extend through a lumen along a length of the catheter shaft.

The hinge can be defined as a preset bend in the lever.

The actuation assembly can include a slidable collar disposed on the lever.

The collar can be slidable between a delivery condition positioned over the hinge to straighten the bend of the lever to the delivery configuration and a deployed condition with the bend exposed to allow the lever to transition to the deployed configuration.

The lever can be made of a super elastic material.

The lever can be configured to incur a strain up to about 8% at the bend.

The actuation assembly can include a transmission member, which can be a rod adapted to slide the collar between the delivery condition and the deployed condition.

The rod can be a hypotube.

The lever can include a varied mechanical property along a length thereof to apply a force of less than about 1.0 lbf to the native leaflet when the lever is transitioned to the deployed configuration.

The varied mechanical property can be selected from a varied thickness or a varied material property.

The varied mechanical property can include a stiffening member along a length thereof.

The lever can be made of a material selected from the group consisting of a metal, a polymer, a composite, or a combination thereof.

The lever can include a wire.

The catheter assembly can further include a leaflet fixation device releasably coupled to the distal portion of the catheter shaft.

The leaflet fixation device can include a first gripper assembly and a second gripper assembly, each gripper assembly configured to capture a respective native leaflet.

As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A catheter assembly with a coaptation aid for repair of leaflets of a heart valve, comprising:
   an elongate catheter shaft having a proximal portion and a distal portion adapted to be positioned transvascularly proximate the heart valve;
   a leaflet fixation device releasably coupled to the distal portion of the catheter shaft;
   a lever having a proximal end and a distal end, the proximal end of the lever being coupled to the distal portion of the catheter shaft at a location proximate to the leaflet fixation device, and a hinge to transition the lever between an elongate delivery configuration generally aligned longitudinally with the distal portion of the catheter shaft and a deployed configuration extending transversely from the distal portion of the catheter shaft, the lever having an atraumatic tip proximate the distal end thereof adapted to contact a distal side of a native leaflet of the heart valve when the distal portion of the catheter shaft is positioned proximate the heart valve and the lever is in the deployed configuration; and
   an actuation assembly coupled to the lever to remotely transition the lever between the delivery configuration and the deployed configuration.

2. The catheter assembly of claim 1, wherein the actuation assembly comprises a transmission member extending along a length of the catheter shaft to remotely transition the lever between the delivery configuration and the deployed configuration.

3. The catheter assembly of claim 2, wherein the transmission member comprises a pull wire to transition the lever from the delivery configuration to the deployed configuration by rotating the lever about the hinge.

4. The catheter assembly of claim 3, wherein the lever is biased toward the delivery configuration.

5. The catheter assembly of claim 3, wherein the pull wire extends through an alignment loop disposed on the distal portion of the catheter shaft.

6. The catheter assembly of claim 3, wherein the pull wire extends through a lumen along a length of the catheter shaft.

7. The catheter assembly of claim 3, wherein the actuation assembly further comprises a linkage coupled to the lever, the pull wire attached to the linkage.

8. The catheter assembly of claim 7, wherein the linkage is coupled to the lever between the hinge and the distal end.

9. The catheter assembly of claim 1, wherein the lever is adapted to apply a force of less than about 1.0 lbf to the native leaflet when the lever is transitioned to the deployed configuration.

10. The catheter assembly of claim 1, wherein the atraumatic tip comprises rounded edges.

11. The catheter assembly of claim 1, wherein the atraumatic tip comprises one or more of nitinol, cobalt chromium, stainless steel, titanium, polyether block amide (PEBAX), polylactic acid (PLA), poly-l-lactide (PLLA), polylactic-co-glycolic acid (PLGA), polyurethane, polyethylene, polyester, and polyamide.

12. The catheter assembly of claim 1, further comprising a second lever coupled to the distal portion of the catheter shaft, the second lever having a proximal end, a distal end, and a hinge to transition the second lever between a delivery configuration and a deployed configuration, the second lever having a second atraumatic tip proximate the distal end of the second lever adapted to contact the distal side of the native leaflet.

13. The catheter assembly claim 12, wherein the actuation assembly comprises a transmission member extending along a length of the catheter shaft to remotely transition the lever and the second lever simultaneously between the delivery configuration and the deployed configuration.

14. The catheter assembly claim 13, wherein the transmission member comprises a pull wire attached to a linkage coupled to both the lever and the second lever to simultaneously transition the lever and the second lever from the delivery configuration to the deployed configuration by rotating each of the lever and the second lever about its respective hinge by application of tension to the pull wire.

15. The catheter assembly claim 13, wherein the pull wire extends through an alignment loop disposed on the distal portion of the catheter shaft.

16. The catheter assembly claim 13, the pull wire extends through a lumen along a length of the catheter shaft.

17. The catheter assembly of claim 1, wherein the hinge is defined as a preset bend in the lever, and further wherein the actuation assembly comprises a slidable collar disposed on the lever, the collar being slidable between a delivery condition positioned over the hinge to straighten the bend of the lever to the delivery configuration and a deployed condition with the bend exposed to allow the lever to transition to the deployed configuration.

18. The catheter assembly of claim 17, wherein the lever is made of a super elastic material.

19. The catheter assembly of claim 17, wherein the lever is configured to incur a strain up to about 8% at the bend.

20. The catheter assembly of claim 17, wherein the actuation assembly comprises a transmission member, the transmission member is a rod adapted to slide the collar between the delivery condition and the deployed condition.

21. The catheter assembly of claim 20, wherein the rod is a hypotube.

22. The catheter assembly of claim 17, wherein the lever comprises a varied mechanical property along a length thereof to apply a force of less than about 1.0 lbf to the native leaflet when the lever is transitioned to the deployed configuration.

23. The catheter assembly of claim 17, wherein the varied mechanical property is selected from a varied thickness or a varied material property.

24. The catheter assembly of claim 17, wherein the varied mechanical property comprises a stiffening member along a length thereof.

25. The catheter assembly of claim 1, wherein the lever is made of a material selected from the group consisting of a metal, a polymer, a composite, or a combination thereof.

26. The catheter assembly of claim 25, wherein the lever comprises a wire.

27. The catheter assembly of claim 1, wherein the leaflet fixation device comprises a first gripper assembly and a second gripper assembly, each gripper assembly configured to capture a respective native leaflet.

* * * * *